United States Patent [19]

Fischer et al.

[11] Patent Number: 5,752,663
[45] Date of Patent: May 19, 1998

[54] MICRO CONCENTRIC TUBE NEBULIZER FOR COUPLING LIQUID DEVICES TO CHEMICAL ANALYSIS DEVICES

[75] Inventors: Steven M. Fischer, Hayward; Paul C. Goodley, Cupertino, both of Calif.

[73] Assignee: Hewlett-Packard Company, Palo Alto, Calif.

[21] Appl. No.: 592,040

[22] Filed: Jan. 26, 1996

[51] Int. Cl.⁶ .................................................. B05R 7/06
[52] U.S. Cl. ................................. 239/424; 73/864.81
[58] Field of Search ................................. 239/423, 424, 239/290; 422/50–104; 73/864.81

[56] References Cited

U.S. PATENT DOCUMENTS

| | | | |
|---|---|---|---|
| 3,889,538 | 6/1975 | Fingerle | 73/864.81 X |
| 4,403,520 | 9/1983 | Sisti et al. | 73/864.81 |
| 4,851,700 | 7/1989 | Goodley | 250/288 |
| 4,960,991 | 10/1990 | Goodley et al. | 250/281 |
| 5,286,451 | 2/1994 | De Silva et al. | 73/864.81 X |
| 5,322,510 | 6/1994 | Lindner et al. | 239/423 X |
| 5,617,997 | 4/1997 | Kobayashi et al. | 239/424 X |

*Primary Examiner*—Lesley D. Morris

[57] ABSTRACT

A method and apparatus for improving pneumatic nebulization of liquids is taught providing for controllable production of droplet size range generated. The improvement is aimed at nebulizers comprised of concentric tubes, the inner transporting analyte liquid, the outer—inert gas. The improvement comprises altering the outer lip of the free end of the inner tube so as to allow laminar flow of the exiting gas. By alteration of the tip, droplets in a controlled size range can be routinely produced with a minimum of operator adjusting.

12 Claims, 2 Drawing Sheets

MICRO CONCENTRIC TUBE NEBULIZER FOR COUPLING LIQUID DEVICES TO CHEMICAL ANALYSIS DEVICES

FIELD OF INVENTION

This invention relates to pneumatic nebulizer devices, and more particularly to liquid nebulizers adapted for coupling with chemical analyzers such as mass spectrometers or atomic absorption spectrometers.

BACKGROUND

Most sensitive mass analysis of liquid samples depends to a large extent on obtaining very fine droplets of the sample (nebulizing the sample) and then drying the droplets. Many person-years of research have been spent improving nebulizers and attempting to obtain "the perfect spray". The most commonly used nebulizer is based on concentric tubes: an inner tube transporting the liquid sample; the outer tube, gas (commonly helium, nitrogen or argon) under pressure. The two streams meet at the exit orifice where the gas imparts its energy to the formation of fine liquid droplets of small and uniform size, or so it is desired. Unfortunately, controlling the collision of the streams and maximizing the production of fine droplets (as opposed to large droplets, which are not suitable candidates for analysis) is problematic. All too often a sub-population of the droplets produced are too big, thus interfering with the subsequent chemical analysis. Big droplets are not amenable to drying, and if undried droplets enter the analysis system, their presence creates noise and/or reduced signal, leading to poor performance on the part of the analytical instrument.

A method and apparatus is needed for narrowing the range of the size droplets produced by a nebulizer. More specifically, an apparatus that controllably produces droplets that fall substantially within the range amenable to analysis by ICP-MS, APCI-MS, ESI-MS, AA or other analytical techniques requiring a liquid to gas phase state change.

SUMMARY OF THE INVENTION

The invention taught herein provides for a pneumatic nebulizer device capable of generating analyte droplets within a narrow size range. Further, the invention provides for a maximization of optimal range droplet formation under conditions under which the nebulizing gas shifts from high pressure to low pressure. The invention herein also provides for lower noise level and increase signal level (as in APCI-MS).

Briefly, the invention herein comprises a pneumatic nebulizer comprising two concentric tubes wherein the outer lip of the free end of the inner tube is configured to optimally impart energy from the inert gas to the eluent stream exiting the inner tube orifice. In current practice, the inner tube has a blunt or square-tipped free end from which liquid exits. The invention provides an inner tube where the outer lip of the free end is radiused or angled. The detailing of the tip ends as taught in the present invention eliminates large droplets and spiking from the nebulized sample. Liquid droplets produced by the nebulizer taught herein range in size from one to fifteen micrometers in diameter. Such droplets are easily evaporated in a matter of milliseconds without excessive heat. Thus, the analyte is more easily transferred into the analysis system.

DETAILED DESCRIPTION OF THE INVENTION

Figure 1:
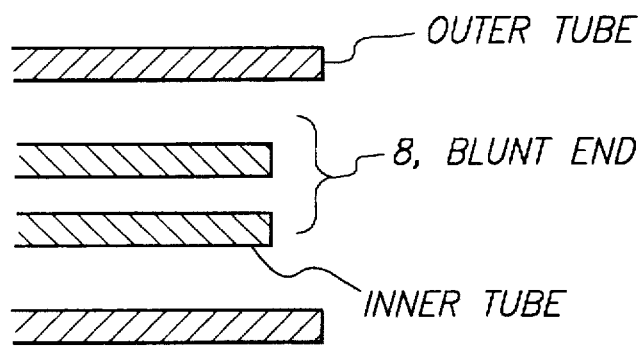
FIG. 1 is a schematic view of prior art.
Figure 2:
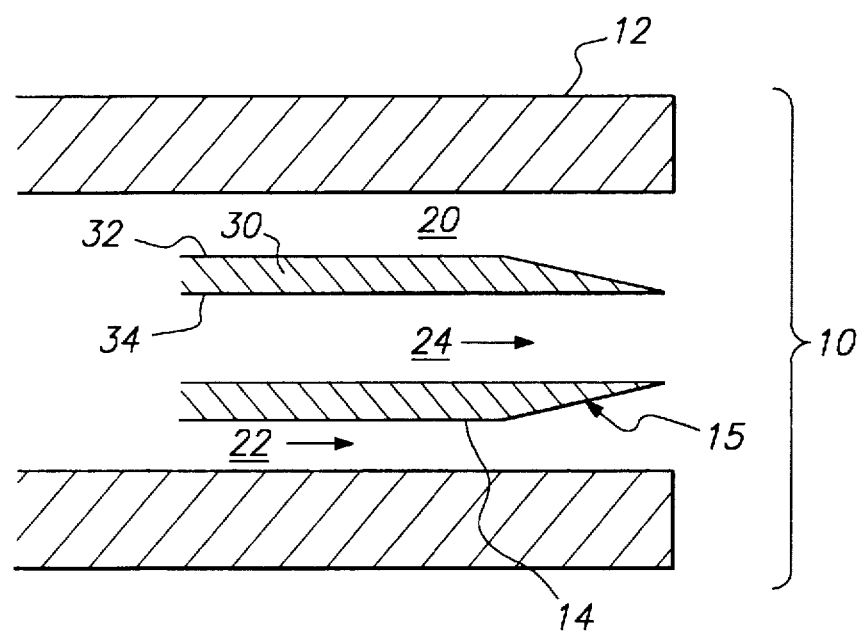
FIG. 2 is a transverse, schematic view of a nebulizer according to the preferred embodiment.

Prior art provided blunt end inner tube (see FIG. 1). The invention, as depicted in FIG. 2, provides a nebulizer 10 comprised of an outer tube 12 and an inner tube 14, each being concentrically configured and positioned along a common axis and each having a free end or tip, and with an annular space 20 between the two tubes. Inner tube 14 has annular wall 30 with outer surface 32 and inner surface 34. The outer lip or annular bevel 15 of the free end of the inner tube 14 is angled at less than 90 degrees, and in the preferred embodiment at about 30 degrees off the horizontal or common center axis. Alternatively, the outer lip of the free end of the inner tube 15 may be radiused (not shown). The angle may be between 5 and 85 degrees.

In the preferred embodiment, the inner tube is a standard 33 gauge needle. The outer tube is 1/16 outer diameter stainless steel tubing with an internal diameter of 0.010 inches.

The angling of the outer lip of the inner tube may be accomplished by any of a number of generally known methods. In the preferred embodiment, a 33 gauge needle was chemically etched to an angle of about 30 degrees.

The nebulizer performs as follows. The liquid 24 exiting the inner tube 14 encounters energized gas 22 exiting the annular space 20. The angled or radiused outer edge of the inner tube exit tip 15 serves to optimize the contact between the two exiting streams. By breaking the edge encountered by the exiting gas, turbulence (and the Bernoulli effect) is reduced. The angling allows the gas to radially vector, thus promoting laminar flow. The result provided by the invention taught herein is droplet formation wherein droplet size is within a range suitable for analysis by the analysis system coupled therewith.

Figure 3:
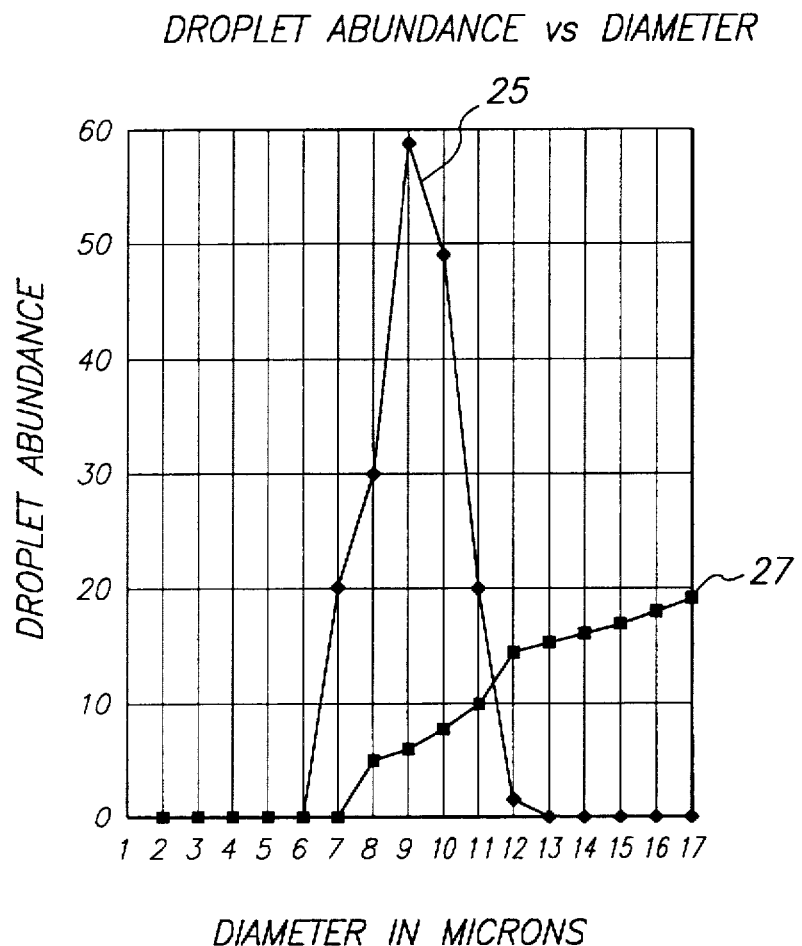
FIG. 3 is a drop size distribution chart representing performance improvement of the preferred embodiment.

Under typical APCI operating conditions of gas and liquid flow on an HP 5989, the preferred embodiment produces a improved droplet size distribution as represented in FIG. 3 by graph line 25. Typical nebulizer droplet size distribution is represented by line 27. The droplet distribution owing to the performance achieved with the nebulizer taught herein corresponds to greater sensitivity in mass spectrometric analysis and a remarkable reduction in noise.

We claim:

1. A pneumatic nebulizer device comprised of an outer and an inner tube being concentrically configured having a first annular space therebetween and positioned along a common center axis and both said tubes having a free end, the inner tube being comprised of a wall with an inner surface and an outer surface, the outer tube having an inner surface, wherein the improvement comprises:

the free end of the inner tube having an annular bevel formed by the outer surface of the wall of the inner tube being angled inwardly toward the common center axis at an angle of less than 90 degrees;

the inner surface of the outer tube having a substantially constant diameter opposite the beveled portion of the outer surface of the inner tube; and a second annular space between the inner surface of the outer tube and the beveled portion of the outer surface of the inner tube having an increasing cross-sectional area in the direction of the free end of the inner tube and the free end of the outer tube.

2. A nebulizer as in claim 1 wherein the inner tube is a 33 gauge needle.

3. A nebulizer as in claim 1 wherein the angle is about 30 degrees.

4. A nebulizer as in claim 1 wherein the angle is between 5 and 85 degrees.

5. A method of nebulizing liquids comprising:

(a) providing a pneumatic nebulizer comprised of concentric inner and outer tubes each having a free end and a common center axis, wherein (I) the inner tube is comprised of a wall with an inner surface and an outer surface and has an outer diameter between about 0.010 and 0.020 inches, (ii) the outer tube having an inner surface and an inner diameter greater than the outer diameter of the inner tube by about one or more hundredths of an inch, and (iii) the free end of the inner tube has an annular bevel formed by the outer surface of the wall of the inner tube being angled inwardly toward the common center axis at an angle of less than 90 degrees, (iv) the inner surface of the outer tube having a substantially constant diameter opposite the beveled portion of the outer surface of the inner tube, (v) an annular space between the inner surface of the outer tube and the beveled portion of the outer surface of the inner tube having an increasing cross-sectional area in the direction of the free end of the inner tube and the free end of the outer tube.

(b) transporting the liquid through the inner tube, (c) transporting a gas under pressure through the outer tube, wherein the liquid and the gas exit the inner and outer tubes, respectively, such that the gas imparts its energy to the formation of fine liquid droplets of small and uniform size.

6. A method as in claim 5 wherein the angle is about 30 degrees.

7. A method as in claim 5 wherein the droplets are within a narrow size range.

8. A method as in claim 5 wherein the angle is between 5 and 85 degrees.

9. A method as in claim 5 wherein the inner tube is a 33 gauge needle.

10. A pneumatic nebulizer device comprising an outer tube and an inner tube wherein (I) the tubes are concentrically configured having a first annular space therebetween and positioned along a common center axis and (ii) both of the tubes have a free end, (iii) the inner tube is comprised of a wall with an inner surface and an outer surface, (iv) the outer tube having an inner surface, (v) the free end of the inner tube has an annular bevel formed by the outer surface of the wall of the inner tube being angled inwardly toward the common center axis at an angle that allows gas exiting the outer tube to radially vector, thereby promoting laminar flow of the gas, (vi) the inner surface of the outer tube having a substantially constant diameter opposite the beveled portion of the outer surface of the inner tube, (vii) a second annular space between the inner surface of the outer tube and the beveled portion of the outer surface of the inner tube having a increasing cross-sectional area in the direction of the free end of the inner tube and the free end of the outer tube.

11. A method of nebulizing liquids comprising:

(a) providing a pneumatic nebulizer comprised of an outer tube and an inner tube wherein (I) the tubes are concentrically configured having a first annular space therebetween and positioned along a common center axis and (ii) both of the tubes have a free end, (iii) the inner tube is comprised of a wall with an inner surface and an outer surface, (iv) the outer tube having an inner surface, (v) the free end of the inner tube has an annular bevel formed by the outer surface of the wall of the inner tube being angled inwardly toward the common center axis at an angle that allows gas exiting the outer tube to radially vector, thereby promoting laminar flow of the gas, (vi) the inner surface of the outer tube having a substantially constant diameter opposite the beveled portion of the outer surface of the inner tube, (vii) a second annular space between the inner surface of the outer tube and the beveled portion of the outer surface of the inner tube having an increasing cross-sectional area in the direction of the free end of the inner tube and the free end of the outer tube.

(b) transporting the liquid through the inner tube, (c) transporting a gas under pressure through the outer tube, wherein the liquid and the gas exit the inner and outer tubes, respectively, such that the gas imparts its energy to the formation of fine liquid droplets of small and uniform size.

12. A method of nebulizing liquids comprising:

(a) providing a pneumatic nebulizer comprised of concentric inner and outer tubes each having a free end and a common center axis, wherein (I) the inner tube is comprised of a wall with an inner surface and an outer surface, (ii) the outer tube having an inner surface and an inner diameter greater than the outer diameter of the inner tube, and (iii) the free end of the inner tube has an annular bevel formed by the outer surface of the wall of the inner tube being angled inwardly toward the common center axis at an angle of less than 90 degrees, (iv) the inner surface of the outer tube having a substantially constant diameter opposite the beveled portion of the outer surface of the inner tube, (v) an annular space between the inner surface of the outer tube and the beveled portion of the outer surface of the inner tube having an increasing cross-sectional area in the direction of the free end of the inner tube and the free end of the outer tube.

(b) transporting the liquid through the inner tube, (c) transporting a gas under pressure through the outer tube, wherein the liquid and the gas exit the inner and outer tubes, respectively, such that the gas imparts its energy to the formation of fine liquid droplets of small and uniform size.

* * * * *